(12) United States Patent
Palti et al.

(10) Patent No.: US 6,402,515 B1
(45) Date of Patent: Jun. 11, 2002

(54) DENTAL IMPLANT WITH VARIABLE PROFILE THREAD

(75) Inventors: Ady Palti, Bruchsal (DE); William R. Wagner, Escondido, CA (US)

(73) Assignee: Sulzer Dental Inc., Carlsbad, CA (US)

( * ) Notice: Subject to any disclaimer, the term of this patent is extended or adjusted under 35 U.S.C. 154(b) by 0 days.

(21) Appl. No.: 09/757,924

(22) Filed: Jan. 10, 2001

(51) Int. Cl.$^7$ ................................................. A61C 8/00
(52) U.S. Cl. ..................................................... 433/174
(58) Field of Search ................................. 433/173, 174

(56) References Cited

U.S. PATENT DOCUMENTS

| | | |
|---|---|---|
| 3,797,113 A | 3/1974 | Brainin |
| 3,849,887 A | 11/1974 | Brainin |
| 4,932,868 A | 6/1990 | Linkow et al. ............. 433/174 |
| 5,007,835 A | 4/1991 | Valen ........................ 433/174 |
| 5,427,527 A | 6/1995 | Niznick et al. ............. 433/174 |
| 5,435,723 A | 7/1995 | O'Brien ..................... 433/174 |
| 5,527,183 A | 6/1996 | O'Brien ..................... 433/174 |
| 5,628,630 A | 5/1997 | Misch et al. ................ 433/174 |
| 5,795,160 A | * 8/1998 | Hahn et al. ................. 433/174 |
| 5,816,812 A | * 10/1998 | Kownacki et al. .......... 433/174 |
| 5,823,777 A | * 10/1998 | Misch et al. ................ 433/174 |
| 5,871,356 A | * 2/1999 | Guedj ........................ 433/174 |
| 5,897,319 A | 4/1999 | Wagner et al. ............. 433/174 |
| 5,967,783 A | * 10/1999 | Ura ............................ 433/174 |
| 6,149,432 A | * 11/2000 | Shaw et al. ................. 433/174 |

* cited by examiner

*Primary Examiner*—Ralph A. Lewis
(74) *Attorney, Agent, or Firm*—Philip S. Lyren (57) ABSTRACT

A dental implant includes a body having a coronal end, and an apical end opposite the coronal end. An implant-prosthetic interface region is provided adjacent the coronal end. A tapered region is adjacent the apical end. A variable profile helical thread extends along the tapered region. The thread includes an apical side, a coronal side and a width defined between the apical and coronal sides. The variable profile thread includes an expanding width in the direction of the coronal end.

18 Claims, 7 Drawing Sheets

DENTAL IMPLANT WITH VARIABLE PROFILE THREAD

BACKGROUND

The disclosures herein relate generally to dental implants and more particularly to a screw form dental implant having a variable profile thread.

Many current screw-form dental implants are well designed for use in dense bone. For example, the implant disclosed in U.S. Pat. No. 5,897,319 has sharp cutting features at their apical ends that readily facilitate self-tapping into hard bone.

The osseous anatomy of the human jaw is complex. While the density of the bone in the anterior regions of the mandible and maxilla is high, the posterior regions, particularly in the maxilla, are of significantly lower density. The height of the bony ridge in the posterior maxilla can be greatly reduced in partially or totally edentulous patients. This can lead to the need for use of shorter dental implants or grafting procedures in the nasal sinus in order to increase the height of bone available for implant placement.

The nasal sinus is lined by a membrane called the nasal or schneiderian membrane. Damage to this membrane during implant placement must be avoided. In the mandible, the mandibular nerve is located within the mandibular canal. Damage to the mandibular nerve must also be avoided. Inadvertent placement of a dental implant into the mandibular canal increases the risk of mandibular nerve damage, particularly if the implant has sharp surfaces at its apical end.

Dental implant stability in low-density bone, such as that found in the posterior regions of the mandible and maxilla, can be difficult to achieve. Compaction of low density bone, such as by the use of osteotomes, is commonly performed in order to enhance the stability of implants at the time of surgical placement. Low density bone can also lead to the problem of placing dental implants too deeply into the jaw, because commonly available implants have a fairly continuous geometric shape, be it cylindrical or tapered, up to the point that is ideally placed at the crest of the bone.

Implants of various tapers and with various thread profiles are known in the art. For example, U.S. Pat. No. 5,427,527 describes a conical implant design that is placed into a cylindrical osteotomy site in order to induce bone compression at the coronal aspect of the implant, i.e. at its widest end.

A variety of thread profiles and patterns are known in the art. The most common design involves a symmetrical, V-shaped appearance such as that illustrated in U.S. Pat. No. 5,897,319. A variable thread profile is disclosed in U.S. Pat. Nos. 5,435,723 and 5,527,183 which is mathematically optimized for stress transfer under occlusal loads. U.S. Pat. Nos. 3,797,113 and 3,849,887 describe dental implants with external thread-like features having a flat shelf facing the coronal end of the implant. U.S. Pat. No. 4,932,868 discloses a thread design with a flat surface disposed toward the apical end of the implant. This thread is not variable over different points of the implant and does not produce both cutting and compression actions as described herein. U.S. Pat. No. 5,007,835 discloses a screw-type dental implant with rounded threads for providing controlled radial osteocompressive force against the walls of a pre-tapped bone site. U.S. Pat. No. 5,628,630 discloses a method for designing dental implants to optimize and control stress transfer to surrounding bone including a thread design that changes from a sharp, highly angled profile at the apical end of the implant to a flat, nearly square profile at the coronal end, the goal being to control the surface area presented to occlusal forces.

Therefore, what is needed is an implant that enhances stability in low density bone such as that formed in the posterior mandible and posterior maxilla.

SUMMARY

One embodiment, accordingly, provides a dental implant that is particularly suited for use in lower density bone. To this end, a dental implant having a variable profile thread includes a body having a coronal end and an apical end. The body includes a tapered region adjacent the apical end. A variable width helical thread extends along the tapered region. The thread has an apical side, a coronal side, and a width defined between the apical and coronal sides. The variable width is expanded in the direction of the coronal end. As a result, the least width of the thread is adjacent the apical end and the greatest width of the thread is adjacent the coronal end.

A principal advantage of this embodiment is that a dental implant is provided that addresses the problems described above. It has a unique combination of implant body and thread profile that enhances stability in low-density bone and considers proximity to the sinus membrane and the mandibular nerve.

DETAILED DESCRIPTION

Figure 1:
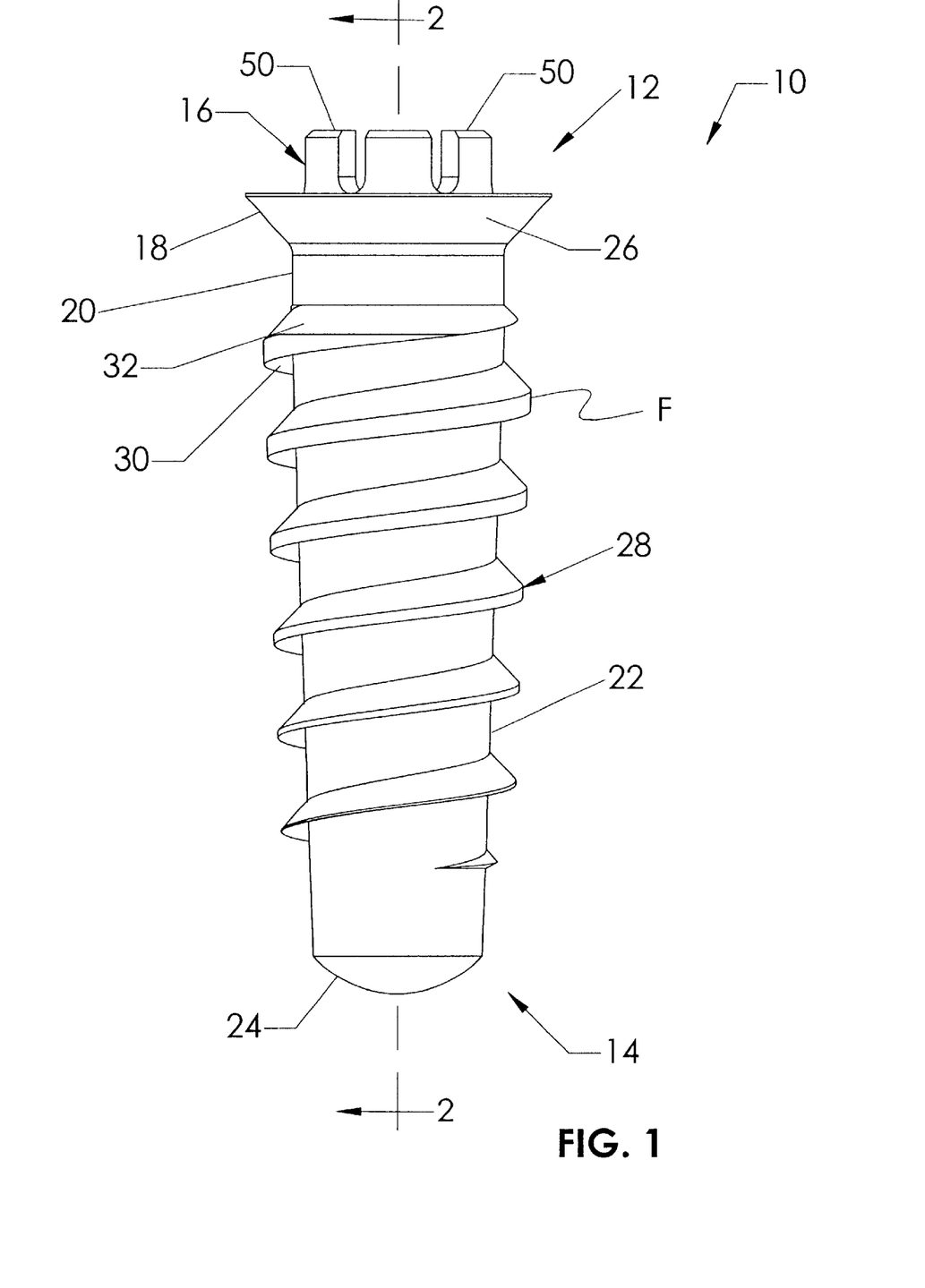
FIG. 1 is a side elevation view illustrating an embodiment of a dental implant of the present invention.
Figure 2:
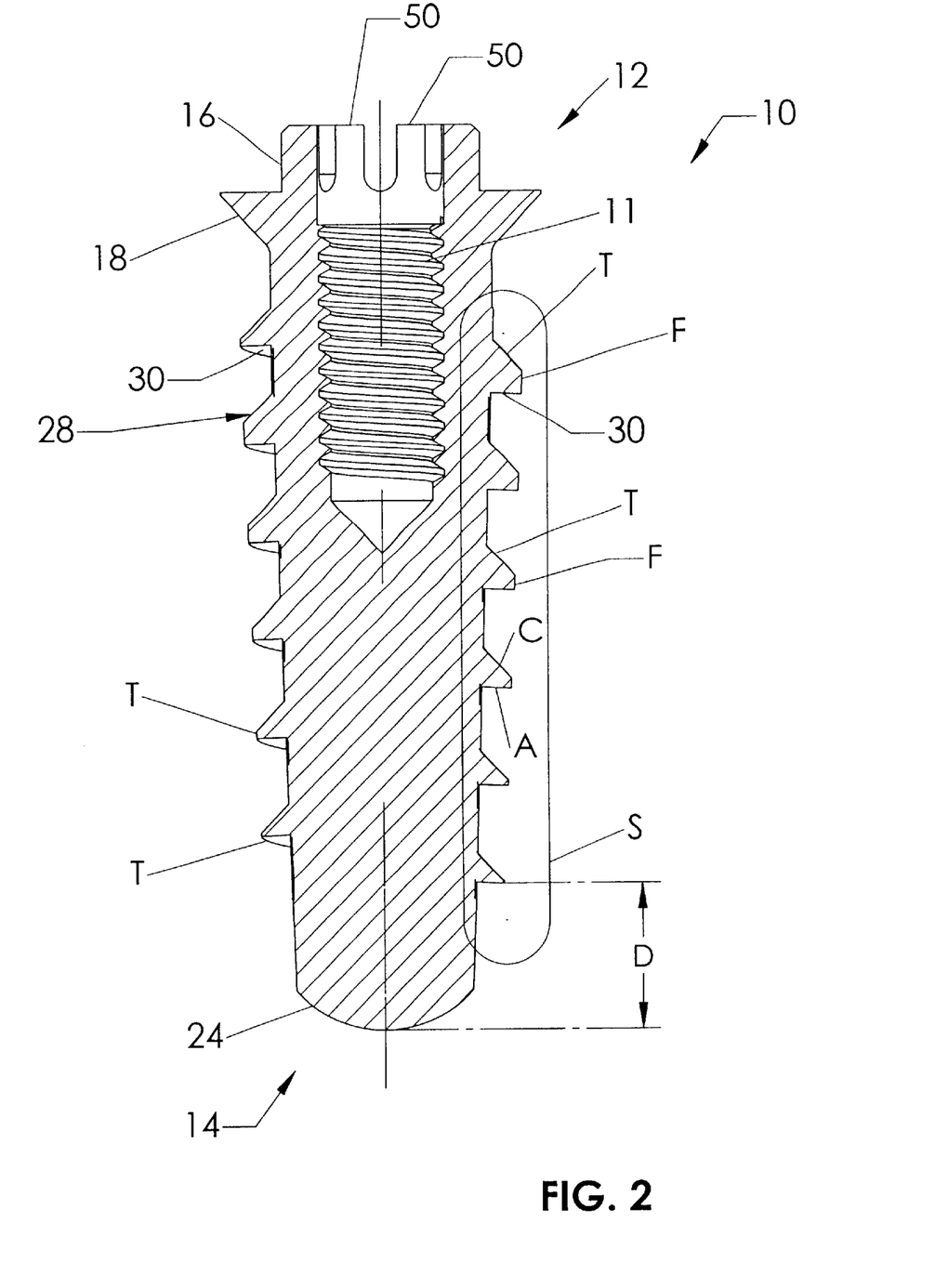
FIG. 2 is a cross-sectional view taken along line 2—2 of FIG. 1.
Figure 5:
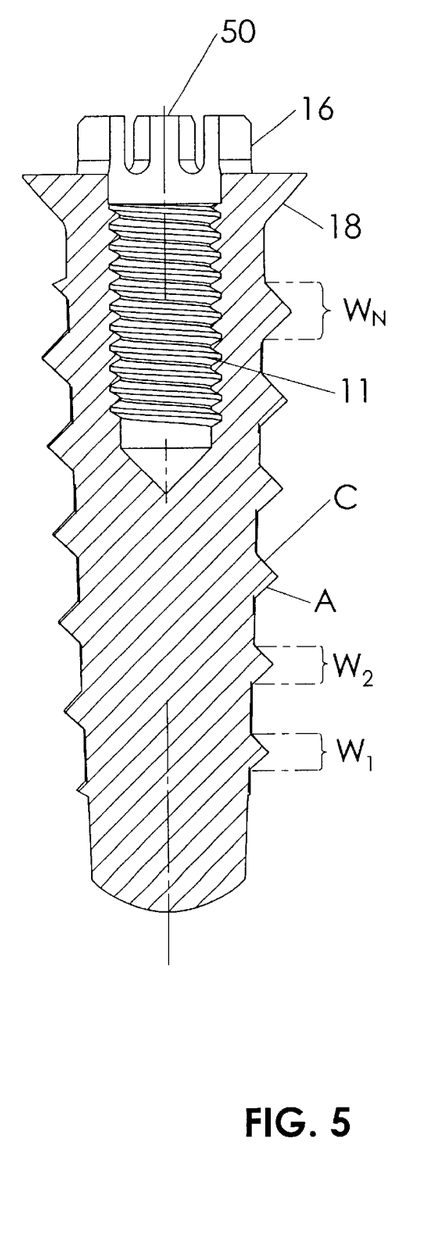
FIG. 5 is a cross-sectional view taken along line 5—5 of FIG. 4.

FIG. 1 illustrates an embodiment of an implant 10 of this disclosure. The implant 10 has a coronal end 12 and an apical end 14. The implant 10 has five distinct regions. At the most coronal aspect is an implant-prosthetic interface region 16. Moving from the coronal to the apical ends is an optional mechanical stop region 18, an optional cylindrical region 20, a tapered region 22, and a rounded end region 24. An internal threaded portion 11, FIGS. 2 and 5, is provided for the attachment of prosthetic components (not shown).

Figure 7:
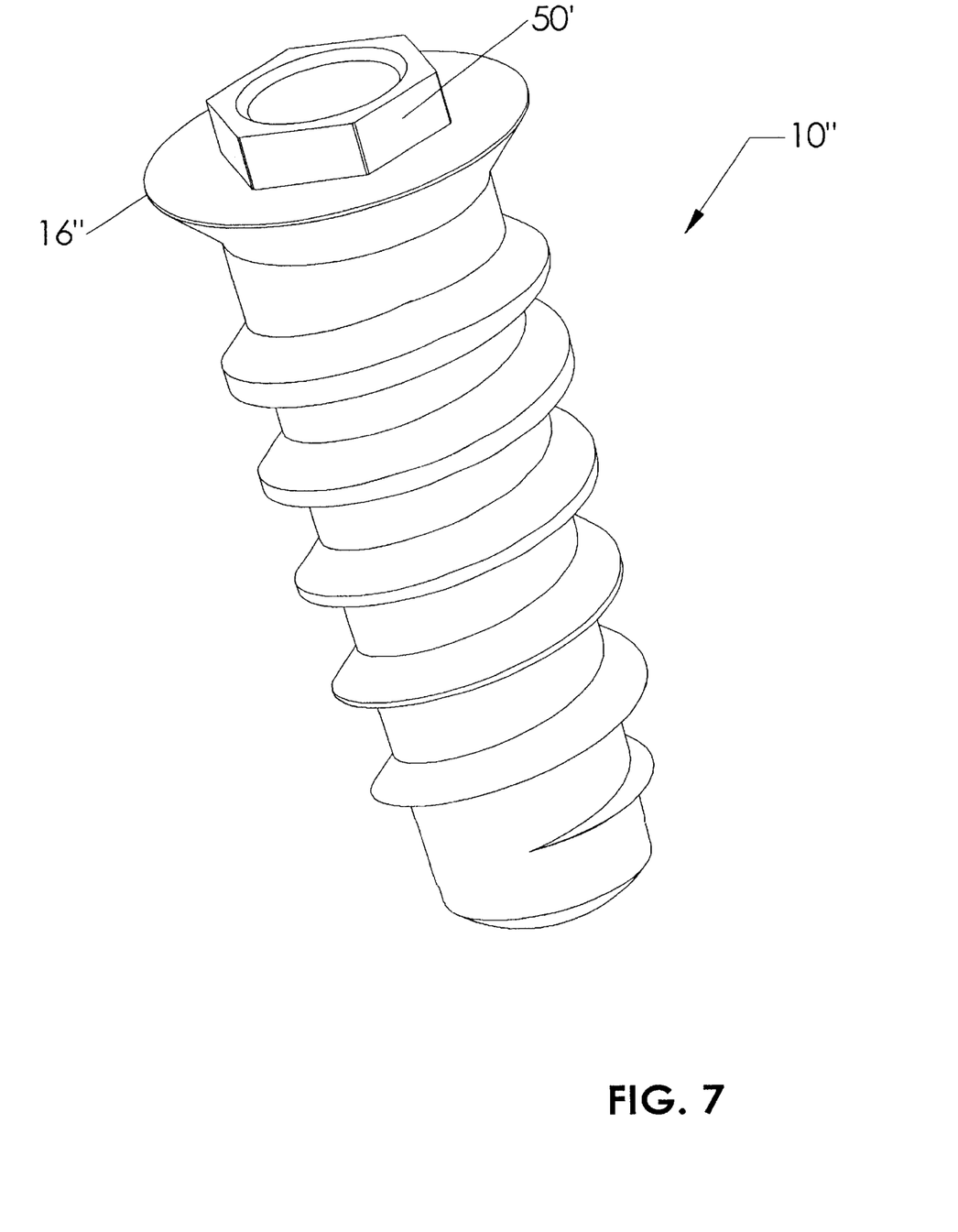

The interface region 16 provides mechanical interlock between the implant 10 and the prosthetic components (not shown) attached to the implant 10. Interface region 16 also provides a means of applying torque to the implant 10 and thus driving the implant 10 into the selected site. The interface region 16 can be any of a number of known interfaces, including external splines 50 or polygons, or internal geometric shapes such as polygons or Morse tapers. An implant 10", FIG. 7, illustrates an example of an external polygon 50', at interface region 16".

The mechanical stop region 18 is sharply tapered so that when the implant 10 is screwed into a prepared osteotomy, a taper 26 limits inadvertently placing the implant 10 too deeply.

The cylindrical region 20 and the tapered region 22 have on their external surfaces a thread 28 of novel profile. The rounded end region 24 has no sharp edges or thread. The external thread 28 includes a progressively changing profile. At the apical end 14, the thread 28 is sharp and narrow in order to facilitate cutting and self-tapping into bone. However, the thread 28 is set back from the apical end 14. As the thread 28 progresses toward the implant coronal end 12, it becomes increasingly broad or wider in cross-sectional profile. The increasing breadth of thread 28 facilitates compression of low-density bone previously tapped by the sharp coronal thread profile. Bone compression increases the stability of the implant 10. In addition, the external thread 28 may have a flat shelf 30 and rounded tip 32, which are most pronounced at the thread's coronal end 12. As the thread 28 progresses from coronal to apical ends, 12 and 14 respectively, of the implant 10, the thread 28 becomes sharper and thinner. The flat shelf 30 provides support against implant micromotion imposed by axial loads, particularly important in low-density bone. Thread 28 is profiled so that a path cut or created in the bone is gradually broadened by compression due to the progressively broader thread 28.

Figure 3:
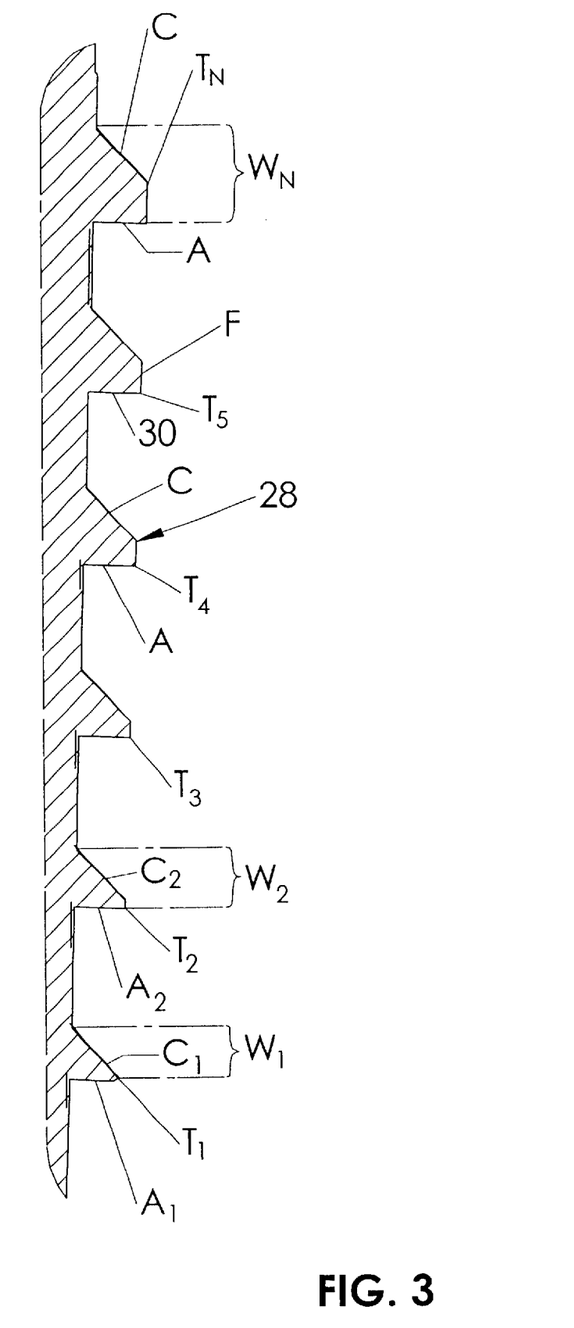
FIG. 3 is a partial section S taken from FIG. 2.

FIGS. 2 and 3 more particularly illustrate the variable profile thread 28. The thread 28 is set back from the rounded end region 24 of the apical end 14 by a distance D. Each turn T of thread 28 is of a different profile from each other turn T of thread 28. For example, implant 10 includes a plurality of turns $T_1$, $T_2$, $T_3$, ... $T_N$. Each turn T includes an apical side A and a coronal side C. A width W is defined between the apical side A and the coronal side C of each turn T. The width varies by being continuously expanded in the direction of the coronal end 12.

Figure 4:
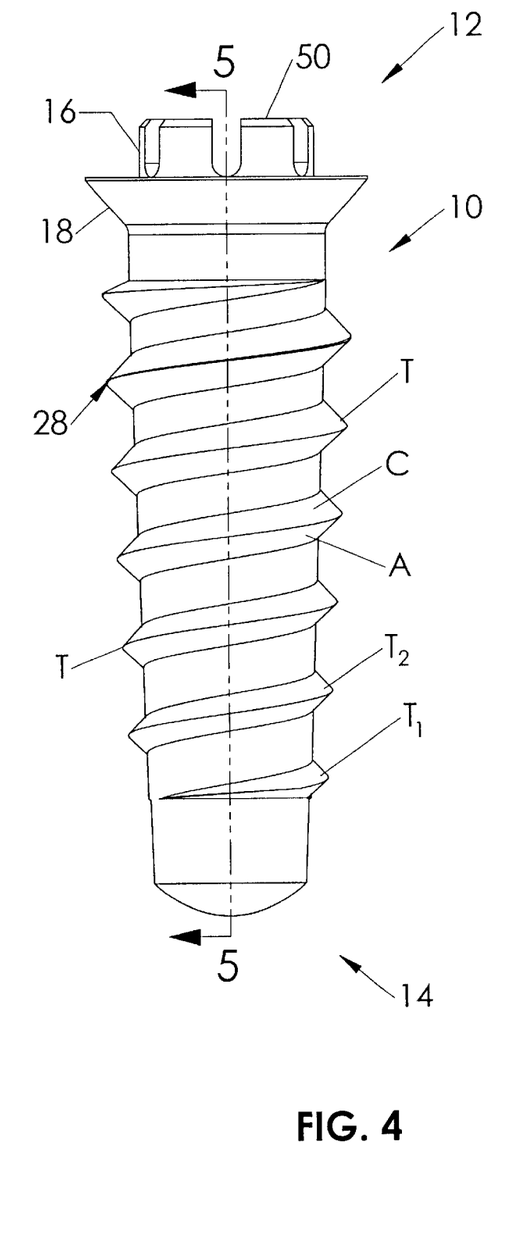
FIG. 4 is a side elevation view illustrating another embodiment of a dental implant of the present invention.

As such, a first turn $T_1$, includes an apical side $A_1$, a coronal side C1, and a width $W_1$. A second turn $T_2$ includes an apical side $A_2$, a coronal side $C_2$, and a width $W_2$. The same pattern is repeated for turns $T_1$, $T_2$, $T_3$, ... $T_N$. so that a least width $W_1$, of the thread 28 is adjacent the apical end 14, and a greatest width $W_N$ is adjacent the coronal end 12. The thread 28 of FIGS. 1–3 includes the flat shelf 30 as discussed above. However, the same variable width pattern discussed above is present in a V-shaped thread as illustrated in FIGS. 4 and 5.

In the embodiment of FIGS. 1–3, a circumferential face F is included on some turns of thread 28. The face F is preferably flat and is not included on the self-tapping portion of the thread 28, adjacent the apical end 14, but is provided as each turn progressively widens toward the coronal end 12. The face F is substantially perpendicular to the shelf 30.

Figure 6:
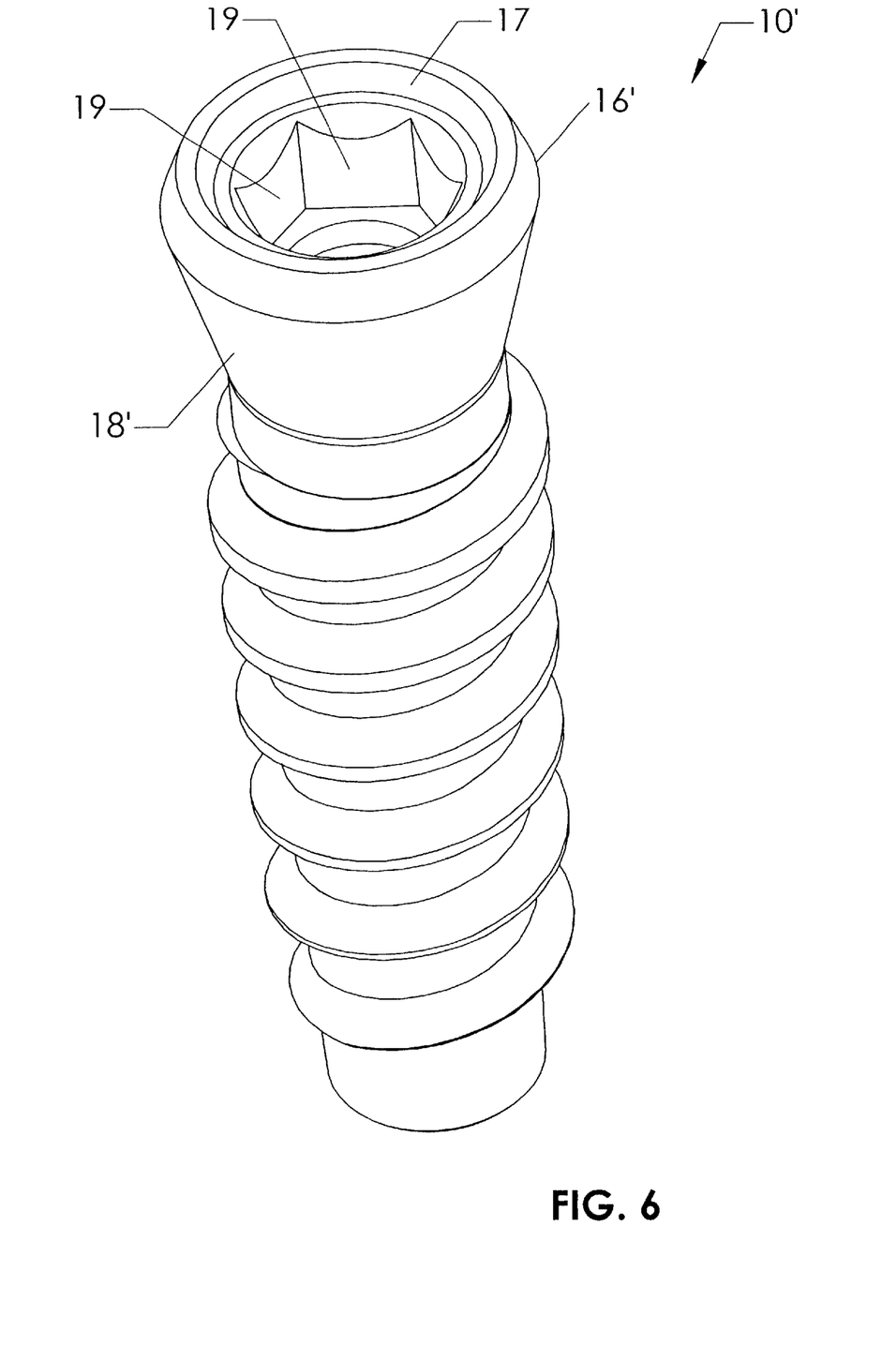
FIG. 6 is an isometric view illustrating a further embodiment of a dental implant of the present invention.
Figure 8:
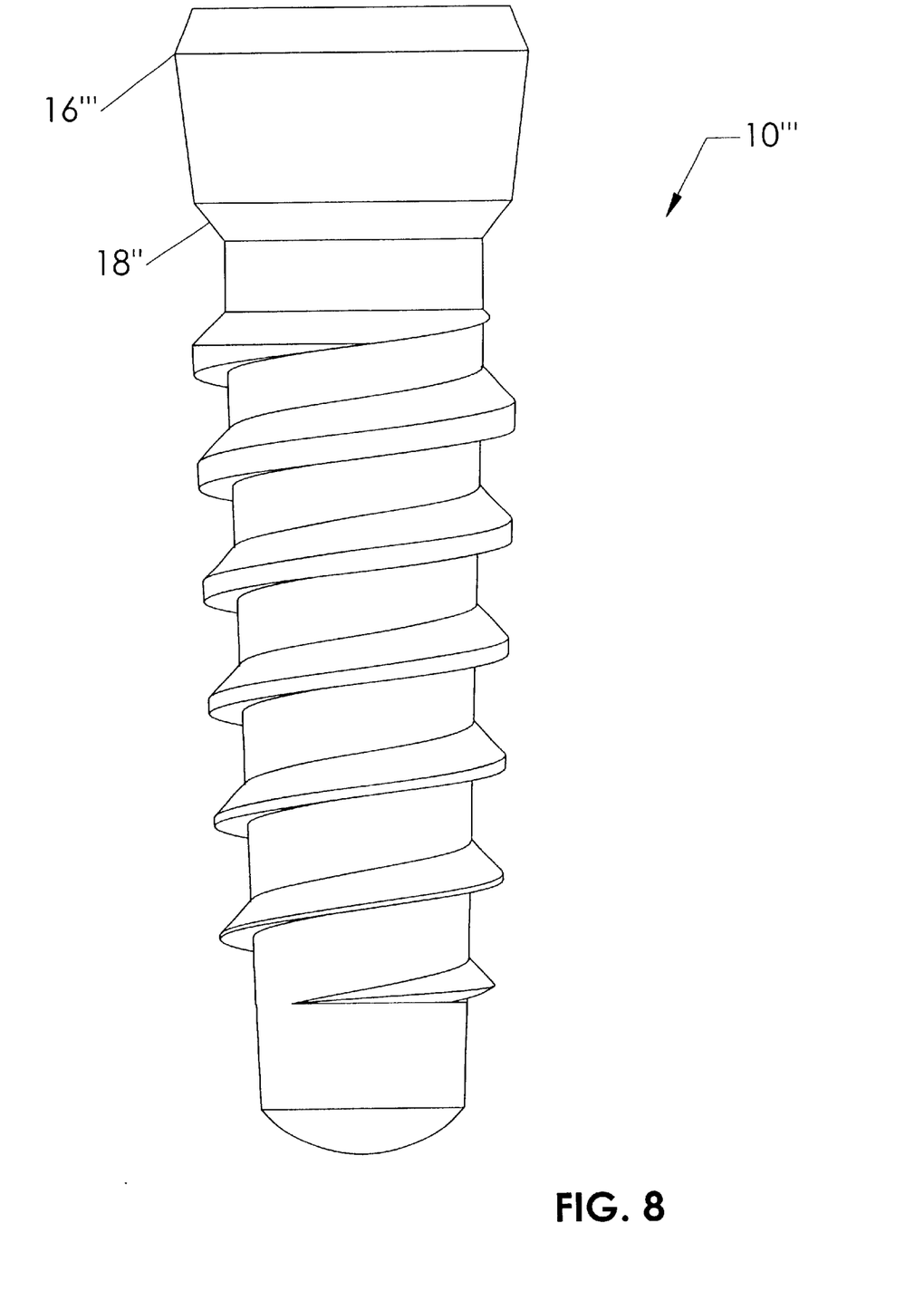

The interface region 16, FIGS. 1, 2, 4 and 5 includes splines 50 whereas, the interface region 16' of a single-stage embodiment 10' of FIG. 6, may optionally include a socket 17 having a plurality of sides 19, e.g. a hex socket. Also, the embodiment of FIG. 6 does not include a sharply tapered mechanical stop as is illustrated at 18 in FIGS. 1, 2, 4 and 5, but instead includes a gradually tapered portion 18'. The gradually tapered portion 18' allows for more freedom in placement depth to adjust the distance that the transgingival collar protrudes from the bone. However, an alternate single-stage embodiment 10''', illustrated in FIG. 8, includes an interface region 16''' including a second angled portion 18'' which acts as a stop.

In operation, the implant can be placed into a pre-drilled osteotomy site that either matches the external diameter of the implant body, that is, the narrowest diameter between threads, or into a site that is narrower than the external diameter of the implant. Placing the implant into a narrower site will provide additional bone compression, and therefore greater initial stability.

As a result, this embodiment provides unique advantages by providing a dental implant fixture particularly suited for use in lower density bone, such as that found in the posterior mandible and maxilla. The implant features a tapered profile and a unique external thread profile that offers superior stability when it is implanted in low density bone. The implant tapers down in diameter beginning at a point about 2–3 mm from below the top surface of the implant. The external thread changes profile from the coronal to the apical ends of the implant fixture, having a sharp, narrow profile at the extreme apical end, particularly suited for cutting into non-tapped bone, and having a broad, rounded profile at the coronal end, particularly suited for compression of bone tapped by the thread at the apical end. Further, the thread profile has a flat shelf on its apical aspect, being most pronounced at the coronal end of the implant and being less pronounced at the apical end of the implant. At its coronal end, the implant has a flared region that acts as a mechanical stop, serving to limit over-insertion of the implant into soft bone. At its apical end, the implant has a round, blunt shape and a set-back thread in the event the implant comes in advertent contact with non-osseous structures.

Although illustrative embodiments have been shown and described, a wide range of modification change and substitution is contemplated in the foregoing disclosure and in some instances, some features of the embodiments may be employed without. a corresponding use of other features. Accordingly, it is appropriate that the appended claims be construed broadly and in a manner consistent with the scope of the embodiments disclosed herein.

What is claimed is:

1. A dental implant having a variable profile comprising:
   a body;
   a coronal end of the body;
   an apical end of the body;
   a tapered region adjacent the apical end; and
   a variable width helical thread extending along the tapered region, the thread having an apical side, a coronal side and a width defined between the apical and coronal sides, and the variable width being progressively expanded substantially along the entire threaded region of the implant in the direction of the coronal end, so that a least width of the thread adjacent the apical end and a greatest width of the thread is adjacent the coronal end.

2. The implant as defined in claim 1 wherein the apical side of the thread includes a flat shelf and the width of the thread is further defined by a circumferential face extending between the apical side and the coronal side.

3. The implant as defined in claim 2 wherein the circumferential face has a flat face substantially perpendicular to the flat shelf and wherein the flat face has a width that progressively expands from the apical end toward the coronal end.

4. The implant as defined in claim 3 wherein the flat face narrows at the apical end and becomes sharp and thin.

5. The implant as defined in claim 1 wherein the apical end includes a rounded region.

6. The implant as defined in claim 5 wherein the thread is self-tapping adjacent the apical end.

7. The implant as defined in claim 6 wherein the self-tapping thread is spaced from the rounded region.

8. A bone cutting and compressing dental implant comprising:

a body having a coronal end and an apical end opposite the coronal end;

a variable profile helical thread extending along an outer surface of the body between the apical end and the coronal end, the thread having an apical side, a coronal side, and a width defined between the apical and coronal sides;

a self-tapping region of the thread spaced from the apical end; and a compression region of the thread, the compression region extending from the self-tapping region toward the coronal end, wherein the variable profile of the thread includes an expanding width in the direction of the coronal end and has a height that is substantially constant along substantially the entire outer surface of the body.

9. The implant as defined in claim 8 wherein the apical side of the thread includes a flat shelf.

10. The implant as defined in claim 9 wherein the width of the thread is further defined by a circumferential face extending between the apical side and the coronal side.

11. The implant as defined in claim 10 wherein the circumferential face is substantially perpendicular to the flat shelf.

12. The implant as defined in claim 11 wherein the circumferential face is flat.

13. The implant as defined in claim 8 wherein the thread has a V-shape.

14. A dental implant comprising:

a body;

a coronal end of the body;

an apical end of the body opposite the coronal end;

an implant-prosthetic interface region adjacent the coronal end; and helical thread extending along substantially an entire length of the body, the thread having an apical side, a coronal side and a width defined between the apical and coronal sides, wherein the width of the thread progressively expands from the apical end to the coronal end and wherein the thread has a height that is substantially constant along the length of the body.

15. The implant as defined in claim 14 wherein the body of the implant is tapered and wherein the thread adjacent the apical end is self-tapping and adapted to cut bone.

16. The implant as defined in claim 15 wherein the thread adjacent the coronal end is adapted to compress bone.

17. The implant as defined in claim 16 wherein the thread has a flat shelf generally perpendicular to the body of the implant and has a rounded tip.

18. The implant as defined in claim 17 wherein the thread has a progressively changing profile.

* * * * *